United States Patent [19]
Lehmann et al.

[11] Patent Number: 6,143,883
[45] Date of Patent: Nov. 7, 2000

[54] WATER-SOLUBLE LOW MOLECULAR WEIGHT BETA-GLUCANS FOR MODULATING IMMUNOLOGICAL RESPONSES IN MAMMALIAN SYSTEM

[75] Inventors: Joachim Lehmann, Scottsdale, Ariz.; Rudolf Kunze, Berlin, Germany

[73] Assignee: Marlyn Nutraceuticals, Inc., Scottsdale, Ariz.

[21] Appl. No.: 09/224,145

[22] Filed: Dec. 31, 1998

[51] Int. Cl.[7] ............................... C07H 5/04; C07H 5/06
[52] U.S. Cl. .................... 536/55.3; 536/55.1; 536/123.1; 536/123.12; 536/124; 536/127; 435/7.31; 435/18
[58] Field of Search .................. 536/54, 123.12, 536/123.1, 124, 127, 55.1, 55.3; 514/54; 435/7.31, 18

[56] References Cited

U.S. PATENT DOCUMENTS

| | | | |
|---|---|---|---|
| 4,110,163 | 8/1978 | Hjortshoj et al. | 195/62 |
| 4,804,545 | 2/1989 | Goering et al. | 426/28 |
| 5,200,215 | 4/1993 | Slade et al. | 426/18 |
| 5,576,015 | 11/1996 | Donzis | 424/442 |
| 5,622,939 | 4/1997 | Jamas et al. | 514/54 |

FOREIGN PATENT DOCUMENTS

| | | |
|---|---|---|
| 0634106 B1 | 4/1999 | European Pat. Off. . |
| 98/13056 | 2/1998 | WIPO . |
| 98/50398 | 12/1998 | WIPO . |

OTHER PUBLICATIONS

John A. Bohn et. al, (1–3)–Beta–D–Glucans as Biolgical Repsonse Modifiers: a Review of Structure–Functional Relationships. Carbohydrate Polymers 28 (1995).

Donald J. Carrow, Beta–1,3–Glucan as a Primary Immune Activator, Townsend Letter for Doctors and Patients, Jun. 1996, pp. 2, 3.

Tomoe Hashimoto et. al, Enhanced Production of Inducible Nitric Oxide Synthase by Beta–Glucans in Mice, pp. 131–135, FEMS Immunology and Medical Microbiology 19 (1997).

K.J.Steffens, Persoption–Criticism and Agreement as Based Upon in Vitro and In Vivo Studies on Mammals, pp. 9–21 of the publication "Absorption of Orally Administered Enzymes," Springer–Verlag, Publisher.

M.L.G. Cardner, A Review of Current Knowledge of Gastronintestinal Absorption of Intact Proteins Including Medicinal Preparation of Proteolytic Enzymes, pp. 1–7 of the publication "Absorption of Orally Administered Enzymes," Springer–Verlag, publisher.

*Primary Examiner*—James O. Wilson
*Attorney, Agent, or Firm*—Lorusso & Loud

[57] ABSTRACT

A fractionated, water-soluble, readily absorbable, low molecular weight beta-glucan is usable as an immune-modulator in the mammalian system. A method is disclosed, which produces a fractionated beta-glucan that is water-soluble and has a molecular weight between 1,000 Daltons–30,000 Daltons (1 kD–30 kD) adaptable to affect changes in the immune responses in mammalian systems.

6 Claims, 3 Drawing Sheets

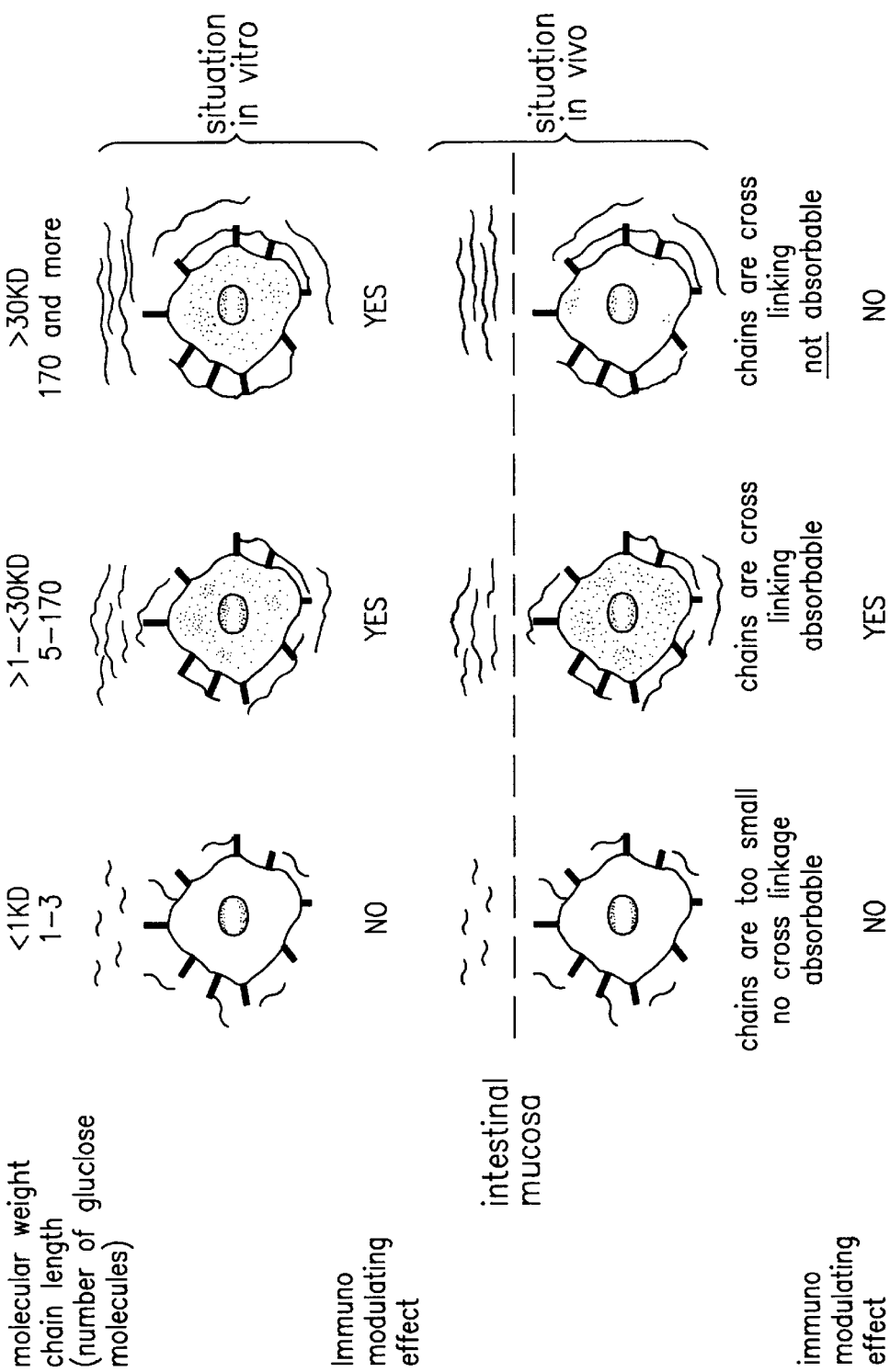

WATER-SOLUBLE LOW MOLECULAR WEIGHT BETA-GLUCANS FOR MODULATING IMMUNOLOGICAL RESPONSES IN MAMMALIAN SYSTEM

BACKGROUND/FIELD OF INVENTION

This invention relates to fractionated, low molecular weight, absorbable beta-glucans. More particularly, this invention relates to a novel method for producing a water-soluble beta-glucan that is adaptable at modulating the immunological responses in mammals.

BACKGROUND OF THE INVENTION

Glucans are important secondary metabolites isolated from plants and micro-organisms. They exhibit prophylactic and therapeutic properties, and can function as biological response modifiers when administered to mammals. As such, glucans have shown beneficial effects in the treatment of infectious and autoimmune diseases, and in clinical management of cancer.

Glucans target various cell types in the immune system, and more particularly macrophages. Previous research has shown that glucans display protective properties against experimentally induced infections in mammalian model systems. Specifically, glucans exert their function on macrophages, monocytes, lymphocytes, and other immune cells in the mammalian system that play a significant role in elicitation of the immune response.

For example, administration of glucans has been shown to significantly enhance the immune system in animals to a wide variety of experimentally induced bacterial, viral, fungal and parasitic infections. Glucans also show strong anti-tumor activity. Glucan carries out its biological function by binding to specific receptor molecules located on the surface of macrophages. In in vitro studies, exposure of these cells to beta-glucans stimulates the immune system. One representative glucan with such immune-enhancing characteristics is branched beta (1,3)-glucan (referred hereinafter to as beta-glucan or β-glucan).

However, a significant impediment to the effective use of beta-glucans as an immune-modulating agent is the rate at which they are absorbed in mammals when orally administered. Naturally occurring beta-glucans contain cross-linked polymers of the basic glucose units and are considered very large molecules. They are insoluble in water and are acid resistant. Thus, when administered orally, they pass through the stomach virtually intact due to their large molecular weight which hinders optimal absorption in the gastrointestinal tract.

Absorbability of these large-molecule beta-glucans is further reduced by the lack of specific enzymes in the gastrointestinal tract to break down large molecular weight, polymeric beta-glucans. It is generally thought that large molecular weight, water-insoluble glucan preparations are unlikely to efficiently bind to its specific receptors and be internalized in the cell at high enough concentrations to be effective as immune-modulators.

Various methods have been disclosed for the extraction and production of beta-glucans adaptable for administration to mammals to affect treatment of diseases. For example, U.S. Pat. No. 5,576,015 discloses the grinding of aqueous-insoluble glucans particulates having reduced sizes in the range of 0.2 to 1 micron. However, the molecular size of the insoluble glucan particulates remains unchanged, i.e., in the range of 3,000,000 Daltons. And the resultant beta-glucans are not watersoluble nor readily absorbable by the mammalian system.

Thus, a low molecular weight, water-soluble beta-glucan is desirable, not only to increase its absorption but also to effectively stimulate the immune response. Accordingly, it would be desirable to have a method for the production of a water soluble beta-glucan with relatively small molecular weight in order to achieve optimal binding to the appropriate receptors and to improve overall absorption in the gastrointestinal tract. In addition, it would be desirable to have a method for the effective use of the small molecular weight beta-glucan as an immune-modulating agent to affect the immunological function in mammals. In particular, it would be desirable to enhance immune function via the induction of cytokines, preferably anti-inflammatory cytokines, by beta-glucan.

SUMMARY OF THE INVENTION

The present invention is directed to the production of a fractionated, water-soluble, readily absorbable, low molecular weight beta-glucan that is usable as an immune-modulator in the mammalian system. A method is disclosed, which produces an improved beta-glucan that is water-soluble and has a molecular weight between 1,000 Daltons–30,000 Daltons (1 kD–30 kD) adaptable to affect the changes in the immune responses in mammals. These and other aspects and advantages of the invention will become apparent from the following detailed description, and the accompanying drawings, which illustrate by way of example the features of the invention.

BRIEF DESCRIPTION OF THE DRAWINGS

FIG. 3 is a conceptual drawing showing the process of contacts between beta-glucans to immunocompetent cells.

DETAILED DESCRIPTION OF THE PREFERRED EMBODIMENTS

Figure 1:
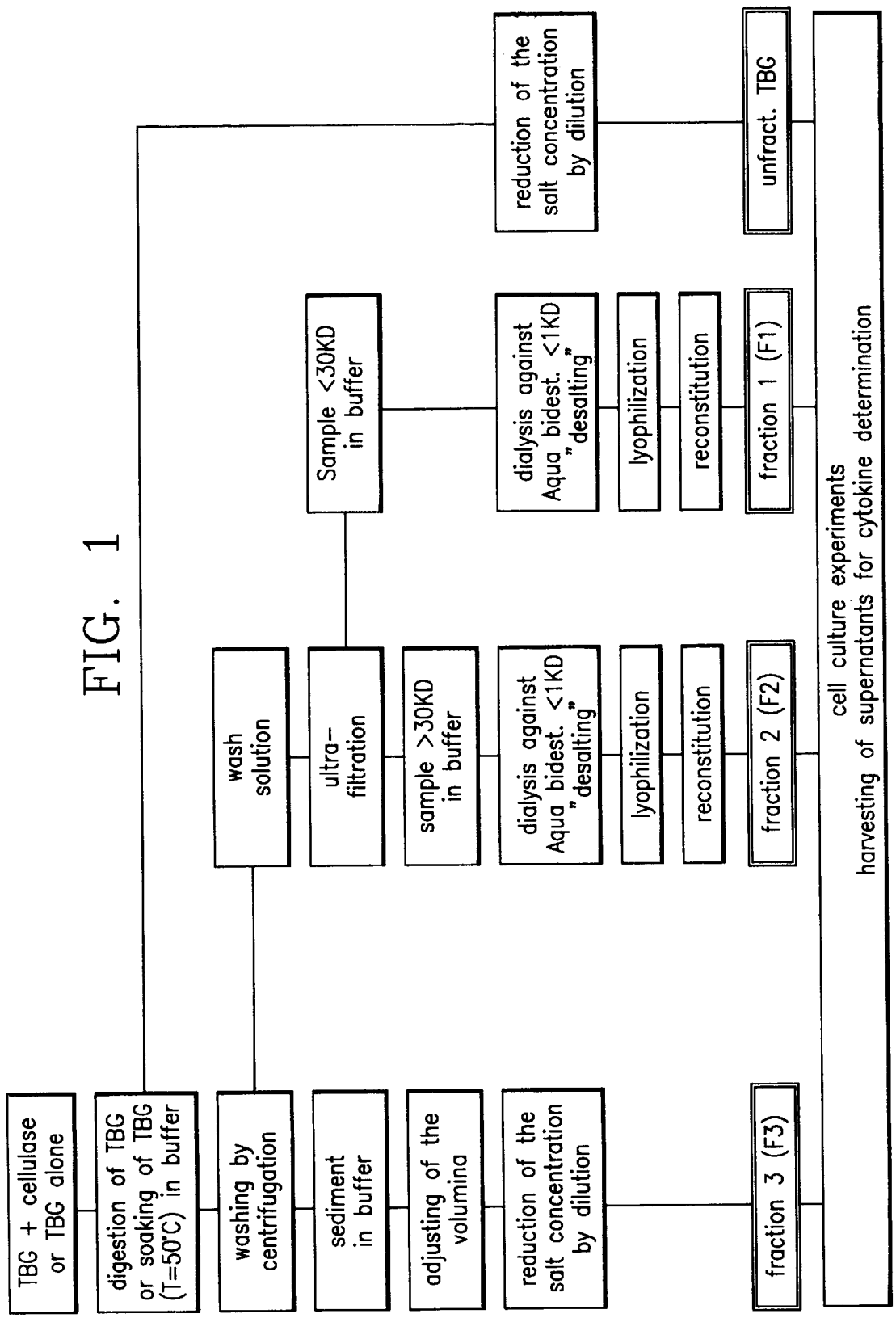
FIG. 1 is a flow chart showing an example for the fractionation and testing of the present inventive and of a native beta-glucan.

The present invention is directed to the production of a fractionated, water-soluble, readily absorbable, low molecular weight beta-glucan that is usable as an immune-modulator in the mammalian system. The method of the production includes the step of enzymatically digesting native beta-glucans with a cellulase to produce a beta-glucan fraction mixture, followed by the step of separating the mixture within designated range of molecular weights and water solubility. The resulting fractionated, low molecular weight, water soluble beta-glucans can then be applied to affect changes in the immune activities in a mammalian system.

To obtain the fractionated, water-soluble, readily absorbable, low molecular weight beta-glucans of the present invention, a native beta glucan is initially prepared as a suspension within an aqueous milieu, such as phosphate-buffered saline (PBS), for a period from approximately 1 to 25 hours.

Following the initial preparation, the beta-glucan is incubated with a cellulase to enzymatically digests or cleaves the large molecules into fractions of various molecular weights. The reaction conditions for the enzymatic digestion are chosen to maximize the fractionalization. Thus for example, the relationship between temperature and the enzymatic activities of a particular commercially available cellulase is generally known to those having ordinary skills in the art, and is available from the commercial suppliers. Accordingly, the optimal temperature used for enzymatic digestion for the present invention will be selected within the range of approximate temperatures at which the cellulase is expected to exhibit the most enzymatic activities. In one example of the present embodiment of the invention, as will be discussed in more detail below, the temperature used in the enzymatic digestion of the native beta-glucan was selected at approximately 50 degrees Celsius, and the incubation period was approximately one hour.

Following the enzymatic digestion, the enzyme-treated beta-glucans are separated according to their molecular weights into water-soluble and water-insoluble fractions. In the present invention, the molecular weight of these fractions were estimated with the use of gel filtration chromatography, where the molecular weight of the soluble fraction of the beta-glucan was estimated to be less than 30,000 Daltons and that of the insoluble fraction was greater than 30,000 Daltons.

Although it has been recognized that large molecular weight beta-glucans are generally water-insoluble and are not readily absorbable, and that low-molecular weight beta-glucan are readily water-soluble, there is no distinct threshold molecular weight of beta-glucans which defines solubility. In the embodiments of the present invention, it has been observed that optimum absorption and cytokine inducing characteristics are best exhibited by a beta-glucan having a molecular weight of less than approximately 30,000 Daltons, and more preferably between 1,000 and 30,000 Daltons (1 kD–30 kD).

Means to achieve separation of a fractionated beta-glucan according to molecular weights are known in the art. Thus, they are not detailed here. By way of example, the enzymatically treated beta-glucans can be fractionated by gel filtration to isolate the insoluble, undigested fraction, which is collected as the sediment, as illustrated in FIG. 1. The solubilized beta-glucan supernatant is then subjected to molecular sieve chromatography to separate a fraction with molecular weight which was less than 30,000 Daltons from the fractions having a molecular weight greater than 30,000 Daltons.

As a further example, a beta-glucan suspension was prepared at a concentration of 50 grams per liter of PBS, which was enzymatically digested at approximately 50 degrees Celsius for 24 hours with a cellulase isolated from Penicillium funiculosum. The cellulase/beta-glucans ratios used in the examples were 1:1000 and 1:5000 by volume. Two commercial forms of beta-glucans were used. The first was a substantially purified beta (1,3) glucan under the designation NSC-24 from Carmel Research, Inc., of Carson City, Nev. The second beta-glucan was obtained from the Takeda Company of Japan (hereinafter referred to as "TBG"). The cellulase used was also available from commercial sources, which are used by the food industry to modify plant food products. For example, a cellulase under the designation of Econase CEP ("Econase") was obtained from Sigma Chemical Co., of St. Louis, Mo.

Following the separation of the fractions of the enzymatically treated beta-glucans as described above, the fractionated, water-soluble, readily absorbable, low molecular weight beta-glucan of the present invention can be prepared for use as an immune-modulator in the mammalian system. Optionally, the inventive product can be lyophilized and reconstituted for later use. Thus, for example, a lyophilized fractionated beta-glucan of the present invention can be placed in a phosphate-buffered saline maintained at a pH value of 7.3 with 100 mM citrate before use.

Cytokine-Inducing Characteristics of the Inventive Fractionated Beta-Glucan.

The water-soluble, readily absorbable, low molecular weight, fractionated beta-glucans of the present invention can be applied to induce expression of cytokines that are conducive to support immune-activities in mammalian systems. These cytokines include interleukins IL-1$\beta$, IL-10, and IL-12, interferon-$\Gamma$ (IFN-$\Gamma$) and tumor necrosis factor-$\alpha$ (TNF-$\alpha$).

In order for the beta-glucans to effectively induce the expression of cytokines, they must be able to interact with their receptors on the cell surface of the mammalian cells. It has been generally recognized that the larger the beta-glucan molecules, the less efficient they will be in binding to the receptors. The beta-glucan obtained as a result of enzymatic digestion of native beta-glucans from the present invention is water-soluble and is within the range of molecular weights that are readily absorbable by the mammalian system.

Figure 2:
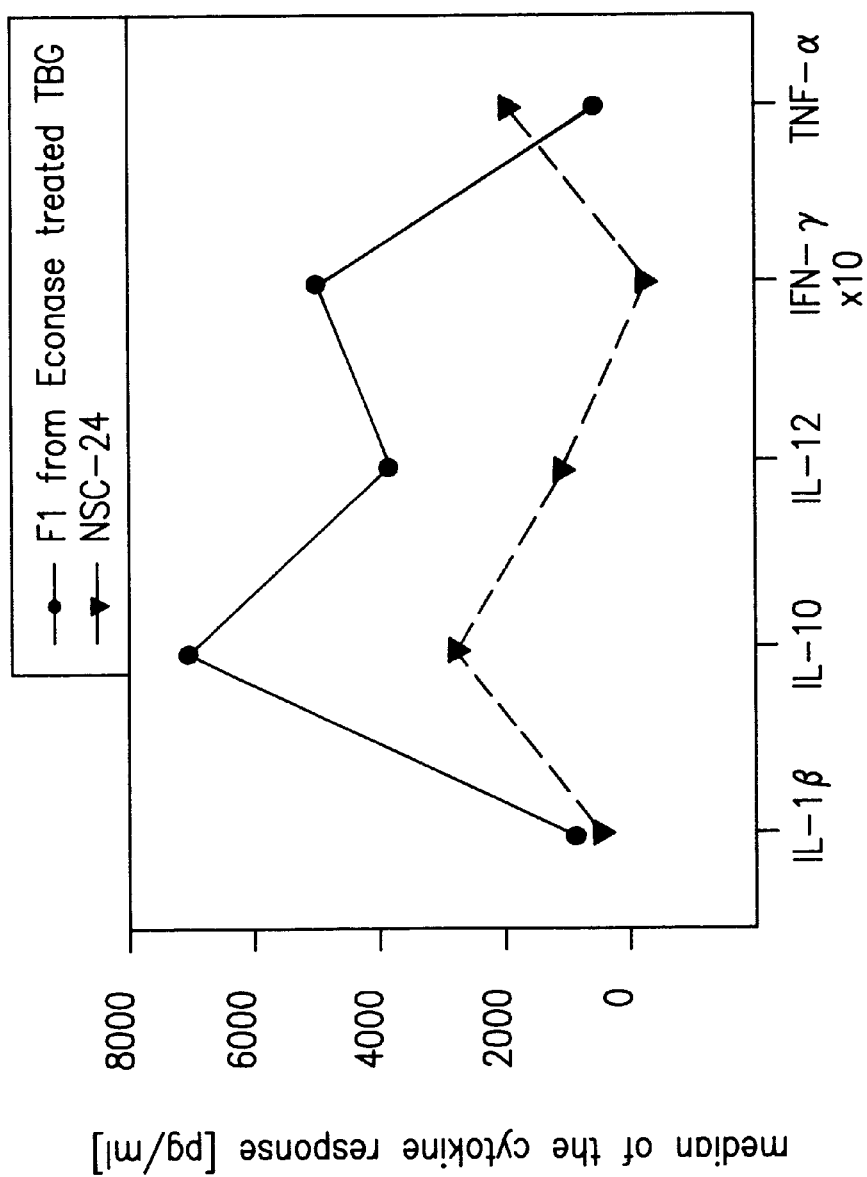
FIG. 2 is a graphical summary of the cytokine profile of the fractionated water-soluble beta-glucan of the present invention in comparison to that of the native beta-glucan.

As shown in FIG. 2, the inventive fractionated, low molecular weight, water-soluble beta-glucan induces the expression of anti-inflammatory cytokines in substantially greater levels than commercially available untreated beta-glucans when applied in a control group for the elicitation of cytokine indication. Further, IFN-$\Gamma$ is induced only by the inventive glucan and not by the untreated beta-glucan.

As shown in FIG. 3, under in vivo conditions, the intestinal mucosa presents a barrier to large molecular weight compounds and, thus, controls the absorption of large molecules, including glucans. It is well known in the art that there is no well-defined molecular weight cutoff for absorption. Beta-glucans with a molecular weight of greater than 30,000 Daltons are expected to be nominally absorbed, but they lack efficiency in the absorption. Compounds with a molecular weight of less than 30,000 Daltons, however, are absorbed better. The inventive fractionated, low molecular weight, water-soluble glucan meets this criterion.

Nutritional Supplementation

The fractionated beta-glucan in the present invention may be taken orally or parenterally to induce the expression of beneficial cytokines in mammalian systems. It is believed that the low molecular weight, fractionated beta-glucan, being water-soluble, is more quickly and efficiently absorbed in the gastrointestinal tract and, consequently, is more beneficial as an immune-modulator as compared to the unfractioned large molecular weight and/or small particle sized native beta-glucan, as illustrated in FIG. 3. The preferred molecular weight to enhance absorption and to induce the expression of beneficial cytokines as immune-modulators is less than approximately 30,000 Daltons, and more preferably between 1,000 Daltons and 30,000 Daltons. Preferred amounts of beta-glucan for nutritional purposes to stimulate the immune system and to induce the expression of beneficial cytokines orally is approximately between 0.2 milligram to about 1.0 milligram per kilogram of body weight of the mammal. For parenteral administration, the dosage ranges from 0.001 milligram to 0.3 milligram per Kilogram of body weight.

Suitable species include fish, crustaceans, domestic farm animals such as hogs, poultry, horses, sheep, and cattle as well as fowl, and humans. The mechanism of action by which beta-glucan stimulates the immune function in mammals is thought to be mediated by the activation of macrophages, thereby stimulating the immune-modulatory potential of the species by expression of beneficial cytokines. By stimulating the immune system in an organism, it can mount an effective resistance against infections by viral, bacterial and, possibly, fungal infections, thus significantly improving the well-being of the mammal.

Topical Applications

The inventive fractionated, low molecular weight, water-soluble glucan may also be combined with a suitable carrier, pharmaceutical or otherwise, for a range of topical applications. Carrier compositions for topical application may include, but may not be limited to, creams, lotions, salves and ointments with appropriate excipients and binders typically contained therein.

In topical applications, it is believed that fractionated, low molecular weight, water-soluble glucan is more efficacious as a dermatological agent. It is also believed that low molecular weight also plays a role in allowing the glucan to remain suspended in a suitable carrier base thereby making glucan more effective as a therapeutic/corrective agent.

Periodontal Applications

As an immune-modulator, fractionated, low molecular weight, water-soluble glucan is anticipated to be of therapeutic value in oral health products including, but not limited to salve, ointment, gel, toothpaste either alone or in conjunction with other antibacterial ingredients of herbal or pharmaceutical origin.

Wound Healing

As a potent booster of the immune system, the inventive fractionated, low molecular weight, water-soluble glucan is anticipated to accelerate wound healing such as, but not limited to, wounds sustained as a result of injury or decreased blood circulation to the extremities in diseases including, but not restricted to, diabetes-induced peripheral neuropathy.

The following examples are not intended to limit the scope of the invention, but are illustrative of various aspects of the invention.

EXAMPLE 1

Preparation of the Inventive Fractionated Glucan

A native, unfractionated beta-glucan was enzymatically digested with a commercially available cellulase by the method described above. The resulting product was fractionated by gel filtration chromatography to obtain the water-soluble immune-modulating fractions with molecular weights ranging from 1,000 to 30,000 Daltons.

After enzymatic digestion with the cellulase, the mixture was fractionated. Each fraction was then desalted by buffer-exchange chromatography, and lyophilized for immunological assays.

EXAMPLE 2

Immunomodulatory Properties of the Inventive Glucan

The inventive fractionated, low molecular weight, water-soluble glucan was used in experiments to measure its potential in inducing the expression of beneficial cytokines that stimulate the immune system. Among the cytokines induced were IL-1$\beta$, IL-10, IL-12, INF-$\Gamma$ and TNF-$\alpha$. FIG. 2 represents a summary of the results from the experiments.

Human peripheral blood mononuclear cells (PBMC's) were harvested according to the established methodology readily known to those with ordinary skills in the art. The cultured PBMC's were exposed to both native, untreated beta-glucan (NSC-24) and the fractionated beta-glucans with a molecular weight between 1 kD to 30 kD that had been obtained from the above referenced Example 1. The experiments were conducted both with and without stimuli, and exposed also to saline to estimate the basal level of immunological activity. The stimuli consisted of a mixture of pokeweed mitgoen, phytohaemagglutinin, concanavalin A and lipopolysaccharide from e. coli. The amount of each cytokine induced was quantified by employing enzyme-linked immuno-sorbent assay (ELISA) kits, which are commercially available.

Aliquots of the PBMC supernatants were taken after 24 and 48 hours of incubation.

Interleukin-1$\beta$ (IL-1$\beta$) 24 Hrs.

Interleukin-10 (IL-10) 24 Hrs.

Interleukin-12 (11-12) 48 Hrs.

Interferon-$\Gamma$ (IFN-$\Gamma$) 48 Hrs.

Tumor Necrosis Factor-$\alpha$ (TNF-$\alpha$) 24 Hrs.

The supernatants of the cell culture were then harvested at appropriate times, aliquoted, prepared and assayed in accordance to methodology and protocols commonly practiced in the art. The concentration of cytokines were determined by a specific ELISA (range of the calibration curve: 8000–125 pg/ml).

The representative test protocol of the determination is described as follows.

1. The antibodies to the individual cytokines and cytokines were reconstituted and stored in accordance to the instructions of the manufacturers.
2. The capture antibody (murine anti human antibody) was diluted in carbonate buffer, pH 9.6, and plated into the wells of a microtiter plate with 50 microliters ($\mu$L) per well (2 mg/ml) for coating. The subsequent incubation (2 hours) took place at room temperature.
3. 100 ml PBS containing 0.1% bovine serum albumin (BSA) were admitted per well and incubated 0.5 h at room temperature.
4. The plate was washed with 3×200 ml per well PBS-Tween (0.05%, Tween in PBST).
5. Thereafter the respective cytokine standards, diluted in cell culture medium, and the probes were tested (50 $\mu$L/well) and incubated for 1 hour at room temperature.
6. The plate was washed with 3×200 ml per well PBST.
7. An antiserum of the goat anti human cytokine antibodies (400 ng/ml) which is conjugated with horseradish peroxidase, was diluted in PBST (50 $\mu$L/well) and incubated for 1 hour at room temperature.
8. The plate was washed with 3×200 ml per well PBST.
9. Thereafter the TMB substrate solution was added to the wells (100 $\mu$L/well). The substrate reaction was stopped by addition of 5 ml H$_2$SO$_4$ (2 N)
10. The optical density was measured (450 nm, MR 5000, Dynatech).

The results of the experiments are summarized in FIG. 2. As shown in FIG. 2, the proinflammatory cytokines IL-1$\beta$ and TNF-$\alpha$ were induced moderately by the fractionated, low molecular weight, water-soluble glucans with a molecular weight between 1 kD to 30 kD, whereas, the anti-inflammatory and regulatory cytokines, IL-10, IL-12 were substantially induced, as well as the interferon-$\Gamma$. In contrast, the native beta-glucans did not show any cytokine induction for IL-1$\beta$ and IFN-$\Gamma$, although cytokine signals were indicated at reduced levels for the IL-10, IL-12.

EXAMPLE 3

Immunomodulatory Potential of the Inventive Glucan

The inventive beta-glucan of the present invention, which is obtained as a result of enzymatic digestion of native β-glucan is low in molecular weight, water-soluble, and is readily absorbable by mammalian system. Further, as shown in FIG. 2, experimental results obtained with the inventive fractionated, low molecular weight, water-soluble beta-glucan show that it induces the expression of anti-inflammatory cytokines in mononuclear cells, which are present in mammalian systems, in greater levels than does commercially available untreated beta-glucan. This cytokine inducing characteristic renders the inventive beta-glucan adaptive for use as a means for modulating the immune responses of a mammalian system. Thus, for example, the inventive beta-glucan can be administered as an immunomodulator to a mammal whose immune responses are monitored or tested. Depending on the level of immune responses measured, more of less amount of the inventive beta-glucan can be applied so as to achieve the desired immune response level.

As referenced above, under in vivo conditions, the intestinal mucosa presents a barrier to large molecular weight compounds and, thus, impedes the absorption of large molecules, including the native glucans. It is well known in the art that there is no well-defined molecular weight cutoff for absorption. Beta-glucans with a molecular weight of greater than 30,000 Daltons are expected to be nominally absorbed, but lacking in efficiency in the absorption. Compounds with a molecular weight of less than 30,000 Daltons, however, are absorbed better. The inventive fractionated, low molecular weight, water-soluble glucan meets this criterion.

From the above, it is apparent that the fractionated beta-glucan produced by the present invention effectively induces various cytokines at levels which are conducive to affect the immune response in mammals. Although native, nonfractionated beta-glucans exhibit immunomodulating characteristics, the fractionated water-soluble, low molecular weight beta-glucan of the present invention clearly demonstrates its superior performance in inducing beneficial cytokines.

While the above description of the invention is directed to the present embodiments or examples of applications, various modifications and improvements can be made without departing from the spirit and scope of the invention.

What is claimed is:

1. A method of producing a water-soluble beta-glucan, which comprises the steps of:
    (a) reacting a branched beta (1–3)-glucan with a cellulase at reaction conditions sufficient to produce a mixture of water-soluble and water-insoluble beta-glucan fractions; and
    (b) separating the beta-glucan mixture according to a pre-determined molecular weight for the water-soluble beta-glucan fraction.

2. The claim according to claim 1, wherein the reaction conditions comprise incubating the beta-glucans with a cellulase at a temperature selected from the range of temperatures at which the cellulase exhibits its highest enzymatic activity.

3. The claim according to claim 1, wherein the reaction conditions comprise incubating the beta-glucan fractions with a cellulase for approximately at least 1 hour.

4. The claim according to claim 1, wherein the pre-determined molecular weight for the water-soluble beta-glucan fraction to be separated from the mixture is between 1,000 Daltons to 30,000 Daltons.

5. The claim according to claim 1, wherein the cellulase to beta-glucans ratio is between 1:1000 to 1:5000 by volume.

6. A method according to claim 1 additionally comprising isolating said cellulase from *Penicillium funiculosum*.

* * * * *